US008367976B2

(12) United States Patent  
Beer et al.

(10) Patent No.: US 8,367,976 B2  
(45) Date of Patent: Feb. 5, 2013

(54) LASER HEATING OF AQUEOUS SAMPLES ON A MICRO-OPTICAL-ELECTRO-MECHANICAL SYSTEM

(75) Inventors: Neil Reginald Beer, Pleasanton, CA (US); Ian Kennedy, Davis, CA (US)

(73) Assignees: Lawrence Livermore National Security, LLC, Livermore, CA (US); The Board of Regents, The University of California, Oakland, CA (US)

( * ) Notice: Subject to any disclaimer, the term of this patent is extended or adjusted under 35 U.S.C. 154(b) by 1091 days.

(21) Appl. No.: 12/331,487

(22) Filed: Dec. 10, 2008

(65) Prior Publication Data  
US 2009/0261086 A1 Oct. 22, 2009

Related U.S. Application Data

(60) Provisional application No. 61/038,489, filed on Mar. 21, 2008.

(51) Int. Cl.  
C12M 1/34 (2006.01)  
C12M 3/00 (2006.01)  
G02B 17/00 (2006.01)  
G01N 25/00 (2006.01)  
G01N 31/00 (2006.01)  
G01N 33/53 (2006.01)  
B01J 19/08 (2006.01)  
B01J 19/12 (2006.01)

(52) U.S. Cl. ....... 219/385; 219/428; 219/383; 435/6.12; 435/91.2; 435/287.2; 392/416; 392/418; 392/419; 422/186

(58) Field of Classification Search .................. None  
See application file for complete search history.

(56) References Cited

U.S. PATENT DOCUMENTS

| | | | |
|---|---|---|---|
| 6,833,536 B2* | 12/2004 | Shigeura | 219/385 |
| 7,041,481 B2* | 5/2006 | Anderson et al. | 435/91.2 |
| 7,173,218 B2* | 2/2007 | Shigeura et al. | 219/428 |
| 7,855,069 B2* | 12/2010 | Lee et al. | 435/287.2 |
| 7,901,939 B2* | 3/2011 | Ismagliov et al. | 436/4 |
| RE43,365 E * | 5/2012 | Anderson et al. | 435/6.12 |
| 2002/0058332 A1* | 5/2002 | Quake et al. | 435/288.3 |
| 2002/0172969 A1 | 11/2002 | Burns et al. | |
| 2003/0047688 A1 | 3/2003 | Faris et al. | |
| 2004/0007463 A1 | 1/2004 | Ramsey et al. | |
| 2004/0180346 A1* | 9/2004 | Anderson et al. | 435/91.2 |
| 2005/0019902 A1 | 1/2005 | Mathies et al. | |
| 2005/0042639 A1 | 2/2005 | Knapp et al. | |
| 2005/0048581 A1 | 3/2005 | Chiu et al. | |
| 2005/0221339 A1* | 10/2005 | Griffiths et al. | 435/6 |
| 2005/0221373 A1 | 10/2005 | Enzelberger et al. | |
| 2006/0084165 A1* | 4/2006 | Lee et al. | 435/259 |
| 2008/0166793 A1 | 7/2008 | Beer et al. | |
| 2009/0283148 A1* | 11/2009 | Shinoda et al. | 422/68.1 |
| 2010/0330578 A1* | 12/2010 | Duhr et al. | 435/6 |

OTHER PUBLICATIONS

Yung-Chieh Tan, et al, "Monodispersed microfluidic droplet generation by shear focusing microfluidic device", Sensors and Actuators B 114 (2006) 350-356.

* cited by examiner

Primary Examiner — Joseph M Pelham  
(74) Attorney, Agent, or Firm — Eddie E. Scott

(57) ABSTRACT

A system of heating a sample on a microchip includes the steps of providing a microchannel flow channel in the microchip; positioning the sample within the microchannel flow channel, providing a laser that directs a laser beam onto the sample for heating the sample; providing the microchannel flow channel with a wall section that receives the laser beam and enables the laser beam to pass through wall section of the microchannel flow channel without being appreciably heated by the laser beam; and providing a carrier fluid in the microchannel flow channel that moves the sample in the microchannel flow channel wherein the carrier fluid is not appreciably heated by the laser beam.

2 Claims, 8 Drawing Sheets

LASER HEATING OF AQUEOUS SAMPLES ON A MICRO-OPTICAL-ELECTRO-MECHANICAL SYSTEM

CROSS-REFERENCE TO RELATED APPLICATIONS

The present application claims benefit under 35 U.S.C. § 119(e) of U.S. Provisional Patent application Ser. No. 61/038,489 filed on Mar. 21, 2008 entitled "method instantaneous in-line heating of aqueous samples on a micro-optical-electro-mechanical system (MOEMS) device," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND OF THE INVENTION

1. Field of Endeavor

The present invention relates to thermal cycling and more particularly to instantaneous in-line heating of aqueous samples on a micro-optical-electro-mechanical system (MOEMS).

2. State of Technology

Microfluidic devices are poised to revolutionize environmental, chemical, biological, medical, and pharmaceutical detectors and diagnostics. "Microfluidic devices" loosely describes the new generation of instruments that mix, react, count, fractionate, detect, and characterize complex gaseous or liquid-solvated samples in a micro-optical-electro-mechanical system (MOEMS) circuit manufactured through standard semiconductor lithography techniques. These techniques allow mass production at low cost as compared to previous benchtop hardware. The applications for MOEMS devices are numerous, and as diverse as they are complex. Typically these devices employ aqueous solvents as the chemical reaction medium, which may or may not be partitioned into discrete segments either as "slugs" spanning the entire channel or discrete droplets emulsified in a carrier fluid such as oil or other organic non-polar fluids.

As sample volumes decrease, reagent costs plummet, reactions proceed faster and more efficiently, and device customization is more easily realized. By reducing the reactor channel dimensions, supplying the requisite activation thermal energy to drive endothermic reactions on-chip becomes much faster as heat diffusion distance decreases proportional to the channel length and the thermal mass to heat decreases on the order of length cubed. However, current MOEMS fluidic systems have the problem of heating not only the chemical reactor volumes within their channels (whether they be "slugs" or emulsion droplet streams), but also heating the entire substrate which is terribly inefficient for cyclical heating reactions where the heat deposited must then be quickly removed. As the reactions proceed the substrate accumulates heat, and takes much longer to cool down.

The present invention provides a method of instantaneous thermal energy deposition into a the chemical reactor partitions or streams utilizing optical energy from a low power, commercially available $CO_2$ laser which has an ideal wavelength for extremely efficient absorption by $H_2O$ molecules. This method provides a major improvement over prior art microfluidic channel heating methods such as joule-heating from trace resistors sputtered or electron-beamed onto the channel walls during device fabrication. The prior art methods are time-consuming and provide the associated device heat build-up described above. This not only provides the desirable cost incentive, but can cut processing times by an order of magnitude, making popular on-chip process such as Polymerase Chain Reaction (PCR), in vitro protein translation, immunoassay analysis, etc. truly real time. The benefits to bacterial, viral, chemical explosives, and other detection, as well as point-of-care diagnostics, are obvious. Also, the burgeoning field of on-chip synthesis of chemical complexes, nanoparticles, and other novel compounds relies on precise energy deposition which is ideally suited by this method.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method of heating a sample on a microchip. The method includes the steps of providing a microchannel flow channel in the microchip; positioning the sample within the microchannel flow channel, providing a laser that directs a laser beam onto the sample for heating the sample; providing the microchannel flow channel with a wall section that receives the laser beam and enables the laser beam to pass through wall section of the microchannel flow channel without being appreciably heated by the laser beam; and providing a carrier fluid in the microchannel flow channel that moves the sample in the microchannel flow channel wherein the carrier fluid is not appreciably heated by the laser beam. In one embodiment the step of providing a laser that directs a laser beam onto the sample for heating the sample provides a laser that directs a laser beam with optical energy absorption in the infra-red region of 1 to 11 µm optical absorption range onto the sample for heating the sample.

The present invention also provides a micro-optical-electro-mechanical system apparatus for heating a sample including a microchip; a microchannel flow channel in the microchip, the microchannel flow channel containing the sample; a laser that directs a laser beam onto the sample for heating the sample; a wall section of the microchannel flow channel that receives the laser beam and enables the laser beam to pass through wall section of the microchannel flow channel, the wall section of the microchannel flow channel being made of a material that is not appreciably heated by the laser beam; a carrier fluid within the microchannel flow channel for moving the sample in the microchannel flow channel, the carrier fluid being made of a material that is not appreciably heated by the laser beam; wherein the laser beam passes through wall section of the microchannel flow channel and heats the sample. In one embodiment the laser produces a laser beam with optical energy absorption in the far infra-red region of 1 to 11

µm optical absorption range. In one embodiment an optical lens is positioned between the laser and the wall section of the microchannel flow channel to focus the laser beam to heat the sample.

The present invention has use in a number of applications. For example, the present invention has use in biowarfare detection applications for identifying, detecting, and monitoring bio-threat agents that contain nucleic acid signatures, such as spores, bacteria, viruses etc. The present invention also has use in biomedical applications for tracking, identifying, and monitoring outbreaks of infectious disease including emerging, previously unidentified and genetically engineered pathogens; for automated processing, amplification, and detection of host or microbial and viral DNA or RNA in biological fluids for medical purposes; for high throughput genetic screening for drug discovery and novel therapeutics; and cell cytometry or viral cytometry in fluids drawn from clinical or veterinary patients for subsequent analysis. The present invention has use in forensic applications for automated processing, amplification, and detection DNA in biological fluids for forensic purposes Food and Beverage Safety; and for automated food testing for bacterial or viral contamination; for water and milk supply sampling. The present invention has use in nanoparticle synthesis and microscale chemical processing for chemical processing and assembly of novel nano-structures, probes, and other endothermic reaction products of interest for manufacturing through microfluidic systems.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
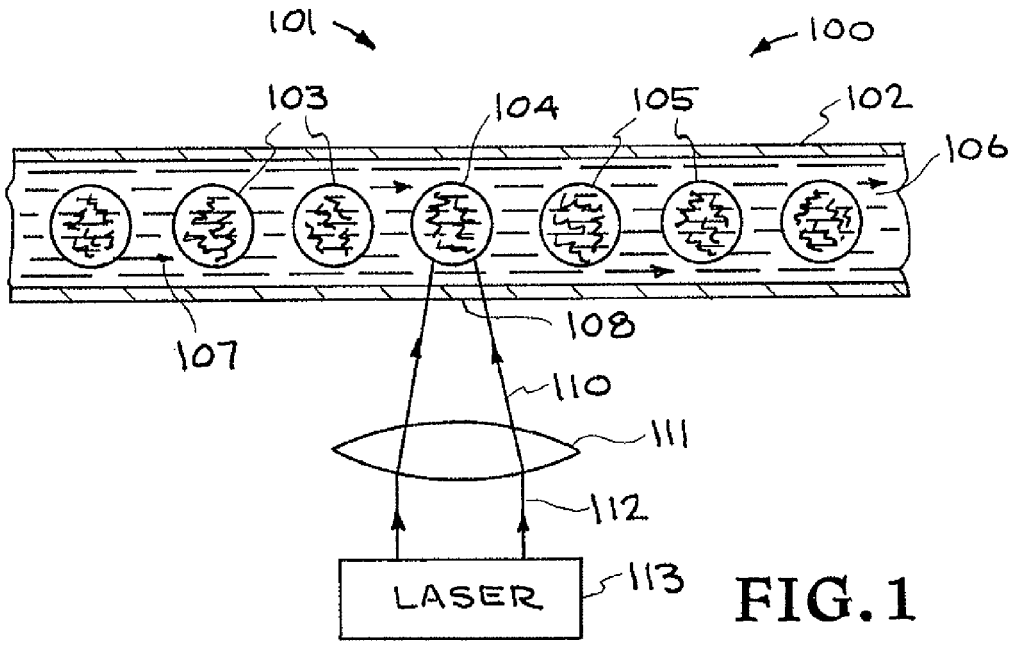
FIG. 1 illustrates one embodiment of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, one embodiment of a system constructed in accordance with the present invention is illustrated. The system is designated generally by the reference numeral 100. The system 100 provides extremely rapid and efficient heating of aqueous solutions within continuous streams or segmented microdroplets on a micro-optical-electro-mechanical system (MOEMS) device 101.

The device 101 includes a microchannel flow channel 106. The microchannel flow channel 106 is contained within silicon or glass device walls 102. A carrier fluid source introduces a carrier fluid 107 into the microchannel flow channel 106. The carrier fluid 107 can be oil, Fluorinert, water, or other carrier fluid 107. The sample to be analyzed is introduced to the microchannel flow channel 106 by a droplet maker or other device that produces droplets or microreactors 103, 104, 105. The sample is contained within the droplets or microreactors 103, 104, 105 and can be bacterial cells, virus particles, nucleic acids, proteins, biomolecules, chemical agents, explosives agents, and other targets of interest. An example of a droplet maker is disclosed in the article, "Monodispersed microfluidic droplet generation by shear focusing microfluidic device," by Yung-Chieh Tan, Vittorio Cristini and Abraham P. Lee, in *Sensors and Actuators,* B: Chemical, Volume 114, Issue 1, 30 Mar. 2006, Pages 350-356. The article, "Monodispersed microfluidic droplet generation by shear focusing microfluidic device," by Yung-Chieh Tan, Vittorio Cristini and Abraham P. Lee, in *Sensors and Actuators*, B. Chemical, Volume 114, Issue 1, 30 Mar. 2006, Pages 350-35 is incorporated herein by reference.

The droplets or microreactors 103, 104, 105 containing the sample are carried to a heating area 108 by the carrier fluid 107. A laser 113 transmits a laser beam 112, 110 through the wall 102 of the microchannel flow channel 106 in the heating area 108. The laser beam 112 from the laser 113 is directed to a lens 111 to focus the laser beam 110 into the microfluidic channel 106 through the wall 102 in the heating area 108. The lens 111 can be circular for spot-focused heating to focus the beam 110 onto the droplet or microreactor 104 containing the sample. The lens 111 can be cylindrical to focus the beam 110 on a line overlaying the entire channel for simultaneous heating of the aqueous contents of the entire channel 106. The silicon or glass wall 102, as well as any non-aqueous sheathing flow, is not appreciably heated.

The carrier fluid 107 moves droplet or microreactor 104 to the heating area 108. In one embodiment the system 100 employs optical energy absorption in the infra-red (IR) region ($\lambda=10.6$ µm) to instantaneously heat fluidic partitions functioning as chemical reactors 103, 104, 105 in the microfluidic device 101. In another embodiment the system 100 employs optical energy absorption in the 3 µm optical absorption range to instantaneously heat fluidic partitions functioning as chemical reactors 103, 104, 105 in the microfluidic device 101. In other embodiments the system 100 employs optical energy absorption in other optical absorption range to instantaneously heat fluidic partitions functioning as chemical reactors 103, 104, 105 in the microfluidic device 101.

An advantage of this system 100 is that the device 102 itself is not heated by the laser 113 beam 112, 110. This is because silicon or glass wall 102 transmits radiation in the IR (and is in fact used as a window in IR devices). Therefore little energy is wasted heating the device and instead is absorbed heating the aqueous solution of interest within the microfluidic device's chambers, channels, or reservoirs. Additionally, many microfluidic devices partition the flow between the aqueous phase and an oil flow, but oil has an absorption 5 orders or more of magnitude lower than water due to the extremely low absorption of oil in the IR. Therefore the carrier fluid for partitioning the chemical reactors in microfluidic devices is not heated by the laser source, and subsequently can immediately cool the fluid droplet or slug as soon as the laser is switched off, attenuated, or blocked by mechanical means. Thus a chilled oil stream with interspersed droplets or slugs can be a highly efficient thermal cycler, operating at speeds orders of magnitude better than what is capable today.

The quantitative basis for this efficient heating is illustrated by an example. At a wavelength of 10.6 µm, the absorption coefficient for water is K-1000 cm$^{-1}$. For oil, K~0.01 cm$^{-1}$, a full 5 orders of magnitude lower. Following Beer's Law:

$$\frac{I_x}{I_0} = e^{(-Kl)} \quad \text{[Equation 1]}$$

$$\text{Absorption} = 1 - e^{(-Kl)}$$

Where K is the absorption coefficient, l is the path length the light travels in cm, and $I_x/I_0$ is the ratio of transmitted to incident radiation, the transmission. Absorption equals 1 minus transmission (assuming negligible reflection).

Thus a commercially available laser, such as a Synrad $CO_2$ laser with a 3.5 mm beam diameter emitting in the far IR at $\lambda$=10,600 nm would excite the strongly absorbing O—H bond of the water molecules within the droplets, slugs, or continuous aqueous stream and provide excellent instantaneous heat deposition. Assuming a channel width of 50 µm for slug flow or a droplet width of 50 µm for a microdroplet-generated emulsion, the following calculations are obtained.

$$\frac{I_x}{I_0} = e^{(-Kl)} = e^{(-1000 \cdot 50 \times 10^{-4})} = 0.0067 \quad \text{[Equation 2]}$$

$$\text{Absorption} = 1 - e^{(-Kl)} = 0.9933$$

$$\therefore I_{absorbed} = 0.9933 I_0 = 1.033 \cdot 10^6 \frac{W}{m^2}$$

$$\therefore P_{absorbed} = I_{absorbed} \cdot A_{droplet} = 1.29 \text{ mW}$$

$$A_{droplet} = \pi r^2 = 1.25 \cdot 10^{-9} m^2$$

$$A_{beam} = \pi r^2 = 9.62 \cdot 10^{-6} m^2$$

$$I_0 = \frac{10W}{A_{beam}} = 1.04 \cdot 10^6 \frac{W}{m^2}$$

Thus a 50 pm droplet would absorb 99.33% of the incident beam intensity, easily heating the droplet while the sheath flow and device remain relatively cool. The following computation shows the power required to heat the droplet to the desired temperature:

$$m = \rho V_{droplet} = \rho \frac{4}{3}\pi r^3 \cong 6.53 \cdot 10^{-11} \text{Kg} \quad \text{[Equation 3]}$$

$$\dot{Q} = mC_p \frac{dT}{dt} = 6.53 \cdot 10^{-11} \cdot 4{,}186 \frac{(95-30)}{\frac{3500}{10^4}} = 50.7 \text{ µW}$$

The power required to heat a droplet of that diameter from 30° C. to 95° C. is 50.7 µW whereas the power absorbed by the droplet from the laser would be 1.29 mW. This almost 2 order of magnitude difference demonstrates that the laser provides exceptional power to quickly and effectively heat the entire stream of droplets simultaneously. Furthermore, higher power lasers can be employed allowing instantaneous heating of entire streams of droplets, slugs, or filled channels by simply utilizing a cylindrical lens. The orders of magnitude excess power available will make reflection losses negligible.

Referring again to FIG. 1, the operation of the system 100 will be described. Sheathing fluid and emulsified droplets or slugs 103, 104, 105 are injected into the flow charnel 106 and act as individual chemical reactors. The flow channel 106 employs a laser 113 with a laser beam 112, 110 in the IR, such as a $CO_2$ gas laser ($\lambda$=10.6 µm) and a circular (spherical or aspherical surface) lens or a cylindrical lens 111 to focus the light on a region 108 or the entire channel 106. The laser 113 is operated in continuous mode or pulsed, and delivers enough energy to the aqueous contents of the channel or chambers to instantaneously heat them while not heating any oil, entrapped air, or the silicon or glass substrate 102 itself. The laser 113 can be shuttered and/or Q-switched to stop heating a droplet or droplet stream. This will allow the most efficient, fastest, and best method for energizing chemical reactions in microfluidics, and is far superior to prior art methods such as trace (surface electrical heaters) in the device or block heaters attached to the bottom of the channel.

Figure 2:
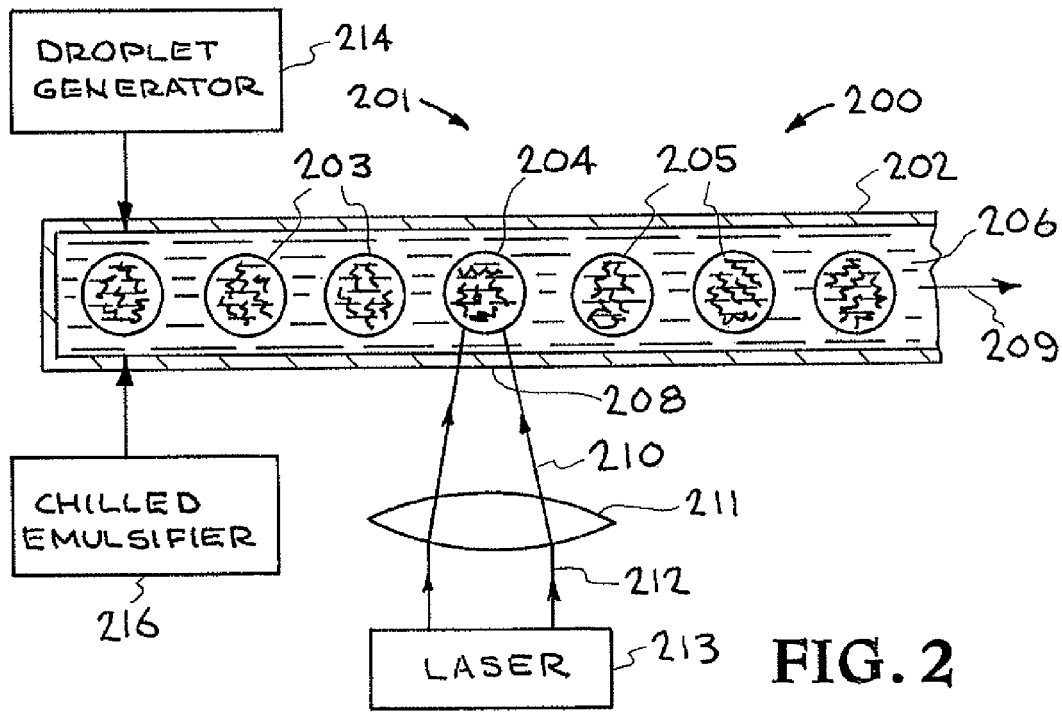
FIG. 2 illustrates another embodiment of the present invention.

Referring now to FIG. 2, another embodiment of a system constructed in accordance with the present invention is illustrated. This system is designated generally by the reference numeral 200. The system 200 provides extremely rapid and efficient heating of a sample in a micro-optical-electro-mechanical system (MOEMS) device 201. The device 201 includes a microchannel flow channel 206. The microchannel flow channel 206 is contained within silicon or glass device walls 202.

The sample to be analyzed is introduced to the microchannel flow channel 206 by a droplet generator or equivalently a droplet maker 214 or other device that produces droplets or microreactors 203, 204, 205. The sample can be bacterial cells, virus particles, nucleic acids, proteins, biomolecules, chemical agents, explosives agents, and other targets of interest. The sample is contained within the droplets or microreactors 203, 204, 205.

The droplet maker 214 produces the droplets or microreactors 203, 204, 205 containing the sample. A chilled emulsifier 216 introduces a carrier fluid 209 into the microchannel flow channel 206. The carrier fluid 209 designated by the arrow moves the droplets or microreactors 203, 204, 205 through the microchannel flow channel 206. The carrier fluid 209 can be oil, fluorinert, water, or other carrier fluid 209.

The droplets or microreactors 203, 204, 205 containing the sample are carried to a heating area 208 by the carrier fluid 209. A laser 213 transmits a laser beam 212, 210 through the wall 202 of the microchannel flow channel 206 in the heating area 208. The laser beam 212 from the laser 213 is directed to a lens 211 to focus the laser beam 210 into the microfluidic channel 206 through the wall 202 in the heating area 208. The lens 211 can be circular with a spherical or aspherical surface for spot-focused heating to focus the beam 210 onto the droplet or microreactor 204 containing the sample. The lens 211 can also be cylindrical to focus the beam 210 on a line overlaying the entire channel for simultaneous heating of the aqueous contents of the entire channel 206. The silicon or glass wall 202, as welt as any non-aqueous sheathing flow, is not appreciably heated.

The structural details of the system 200 having been described, the operation of the system 200 will be explained.

The carrier fluid 209 and emulsified droplets 203, 204, 205 are injected into the flow channel 206 and act as individual chemical reactors. A laser 213 with a laser beam 212, 210 and a circular or spherical lens 211 focuses the light on a region 208 or the entire channel 206. The laser 213 is operated in continuous mode or pulsed, and delivers enough energy to the aqueous contents of the channel or chambers to instantaneously heat them while not heating any oil or non-aqueous carrier fluid, entrapped air, or the silicon or glass substrate 202 itself. The laser 213 can be shuttered and/or Q-switched to stop heating a droplet or droplet stream. This will allow the most efficient, fastest, and best method for energizing chemical reactions in microfluidics, and is far superior to prior art methods such as trace (surface electrical heaters) in the device or block heaters attached to the bottom of the channel.

Figure 3:
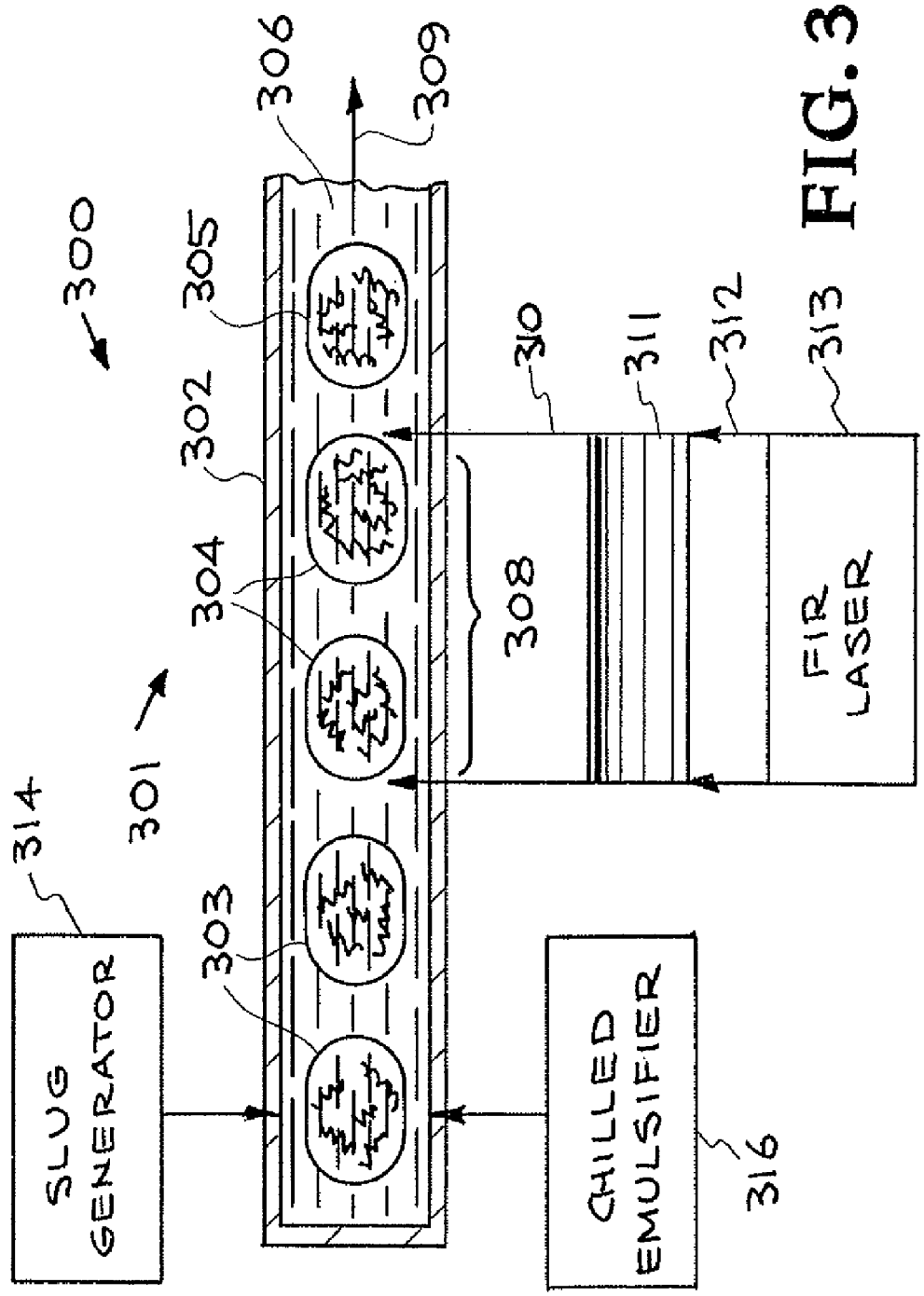
FIG. 3 illustrates yet another embodiment of the present invention.

Referring now to FIG. 3, yet another embodiment of a system constructed in accordance with the present invention is illustrated. This system is designated generally by the reference numeral 300. The system 300 provides extremely rapid and efficient heating of a sample in a micro-optical-electro-mechanical system (MOEMS) device 301. The device 301 includes a microchannel flow channel 306. The microchannel flow channel 306 is contained within silicon or glass device walls 302.

The sample to be analyzed is introduced to the microchannel flow channel 306 by a slug generator 314 or other device that produces slugs or microreactors 303, 304, 305. The sample can be bacterial cells, virus particles, nucleic acids, proteins, biomolecules, chemical agents, explosives agents, and other targets of interest. The sample is contained within the slugs or microreactors 303, 304, 305.

The slug generator 314 produces the slugs or microreactors 303, 304, 305 containing the sample. A chilled emulsifier 316 introduces a carrier fluid 309 into the microchannel flow channel 306. The carrier fluid 309 designated by the arrow moves the slugs or microreactors 303, 304, 305 through the microchannel flow channel 306. The carrier fluid 309 can be oil, Fluorinert, non-polar solvents, organic liquids, or other carrier fluid 309.

The slugs or microreactors 303, 304, 305 containing the sample are carried to a heating area 308 by the carrier fluid 309. A laser 313 transmits a laser beam 312, 310 through the wall 302 of the microchannel flow channel 306 in the heating area 308. The laser beam 312 from the laser 313 is directed to a lens 311 to focus the laser beam 310 into the microfluidic channel 306 through the wall 302 in the heating area 308. The lens 311 focuses the beam 310 on a line overlaying the heating area 308 in the channel 306 for simultaneous heating of the aqueous contents of the area of the channel 306 containing slugs or microreactors 304. The silicon or glass wall 302, as well as any non-aqueous sheathing flow, is not appreciably heated. The lens 311 can also be circular for spot-focused heating.

The structural details of the system 300 having been described, the operation of the system 300 will be explained. The carrier fluid 309 and emulsified slugs 303, 304, 305 are injected into the flow channel 306 and act as individual chemical reactors. A laser 313 with a laser beam 312, 310 and lens 311 focuses the light on a region 308 of the channel 306. The laser 313 is operated in continuous mode or pulsed, and delivers enough energy to the aqueous contents of the channel or chambers to instantaneously heat them while not heating any oil, entrapped air, or the silicon or glass substrate 302 itself. The laser 313 can be shuttered and/or Q-switched to stop heating a droplet or droplet stream. This will allow the most efficient, fastest, and best method for energizing chemical reactions in microfluidics, and is far superior to prior art methods such as trace (surface electrical heaters) in the device or block heaters attached to the bottom of the channel.

Figure 4:
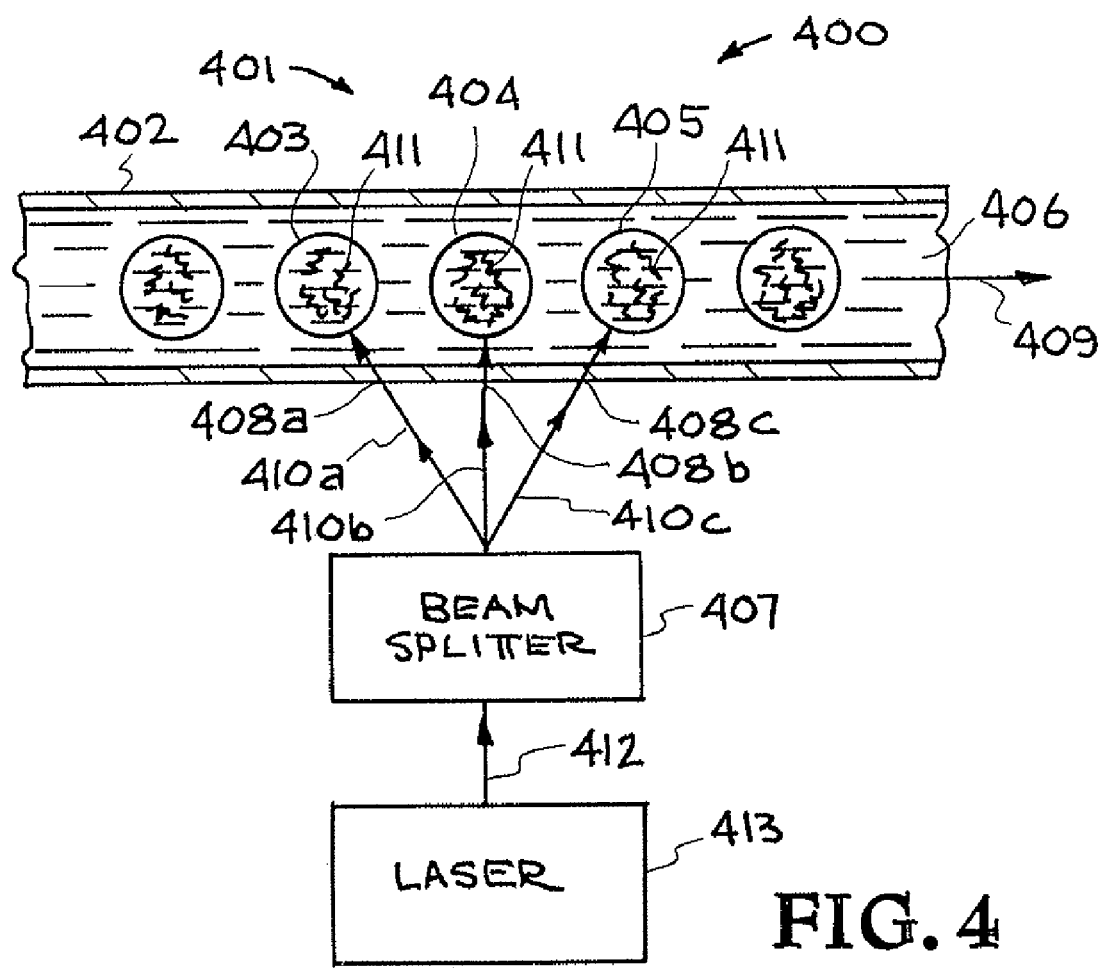
FIG. 4 illustrates another embodiment of the present invention.

Referring now to FIG. 4, another embodiment of a system constructed in accordance with the present invention is illustrated. This system is designated generally by the reference numeral 400. The system 400 provides extremely rapid and efficient heating of a sample 411 in a micro-optical-electro-mechanical system (MOEMS) device 401. The device 401 includes a microchannel flow channel 406. The microchannel flow channel 406 is contained within silicon or glass walls 402.

The sample 411 to be analyzed is introduced to the microchannel flow channel 406 by a droplet maker or other device that produces droplets or microreactors 403, 404, 405. The sample 411 can be bacterial cells, virus particles, nucleic acids, proteins, biomolecules, chemical agents, explosives agents, and other targets of interest. The sample 411 is contained within the droplets or microreactors 403, 404, 405.

The droplet maker produces the droplets or microreactors 403, 404, 405 containing the sample 411. The carrier fluid 409 designated by the arrows moves the droplets or microreactors 403, 404, 405 through the microchannel flow channel 406. The carrier fluid 409 can be oil, Fluorinert, a non-aqueous fluid, non-polar solvents, or other carrier fluid 409. The droplets or microreactors 403, 404, 405 containing the sample 411 are carried to an area where they will be heated by a laser 413.

A laser 413 transmits a laser beam 412 to a beam splitter 407. The beam splitter 407 splits the laser beam 412 into three separate laser beams 410a, 410b, and 410c. The three separate laser beams 410a, 410b, and 410c are directed to the microchannel flow channel 406.

The laser beam 410a is directed through the wall 402 of the microchannel flow channel 406 in a heating area 408a. The laser beam 410a provides spot-focused heating of the droplet or microreactor 403 containing and the sample 411. The silicon or glass wall 402, as well as any non-aqueous sheathing flow, are not appreciably heated by the laser beam 410a.

The laser beam 410b is directed through the wall 402 of the microchannel flow channel 406 in a heating area 408b. The laser beam 410b provides spot-focused heating of the droplet or microreactor 404 containing and the sample 411. The silicon or glass wall 402, as well as any non-aqueous sheathing flow, are not appreciably heated by the laser beam 410b.

The laser beam 410c is directed through the wall 402 of the microchannel flow channel 406 in a heating area 408c. The laser beam 410a provides spot-focused heating of the droplet or microreactor 405 containing and the sample 411. The silicon or glass wall 402, as well as any non-aqueous sheathing flow, are not appreciably heated by the laser beam 410c.

The structural details of the system 400 having been described, the operation of the system 400 will be explained. The carrier fluid 409 and emulsified droplets 403, 404, 405 are injected into the flow channel 406 and act as individual chemical reactors. The laser 413 with laser beam 412 to a beam splitter 407. The beam splitter 407 splits the laser beam 412 into three separate laser beams 410a, 410b, and 410c. The three separate laser beams 410a, 410b, and 410c are directed to the microchannel flow channel 406. The laser beams 410a, 410b, and 410c are directed through the wall 402 of the microchannel flow channel 406 in the heating areas 408a, 408b, and 408c respectively. The laser beams 410a, 410b, and 410c provide spot-focused heating of the droplet or microreactors 403, 404, and 405 and the sample 411. The silicon or glass wall 402, as well as any non-aqueous sheathing flow, are not appreciably heated by the laser beam 410a. The laser 413 is operated in continuous mode or pulsed, and delivers enough energy to the sample 411 instantaneously heat the sample 411 while not heating any oil, entrapped air, or the silicon or glass wall 402.

Figure 5:
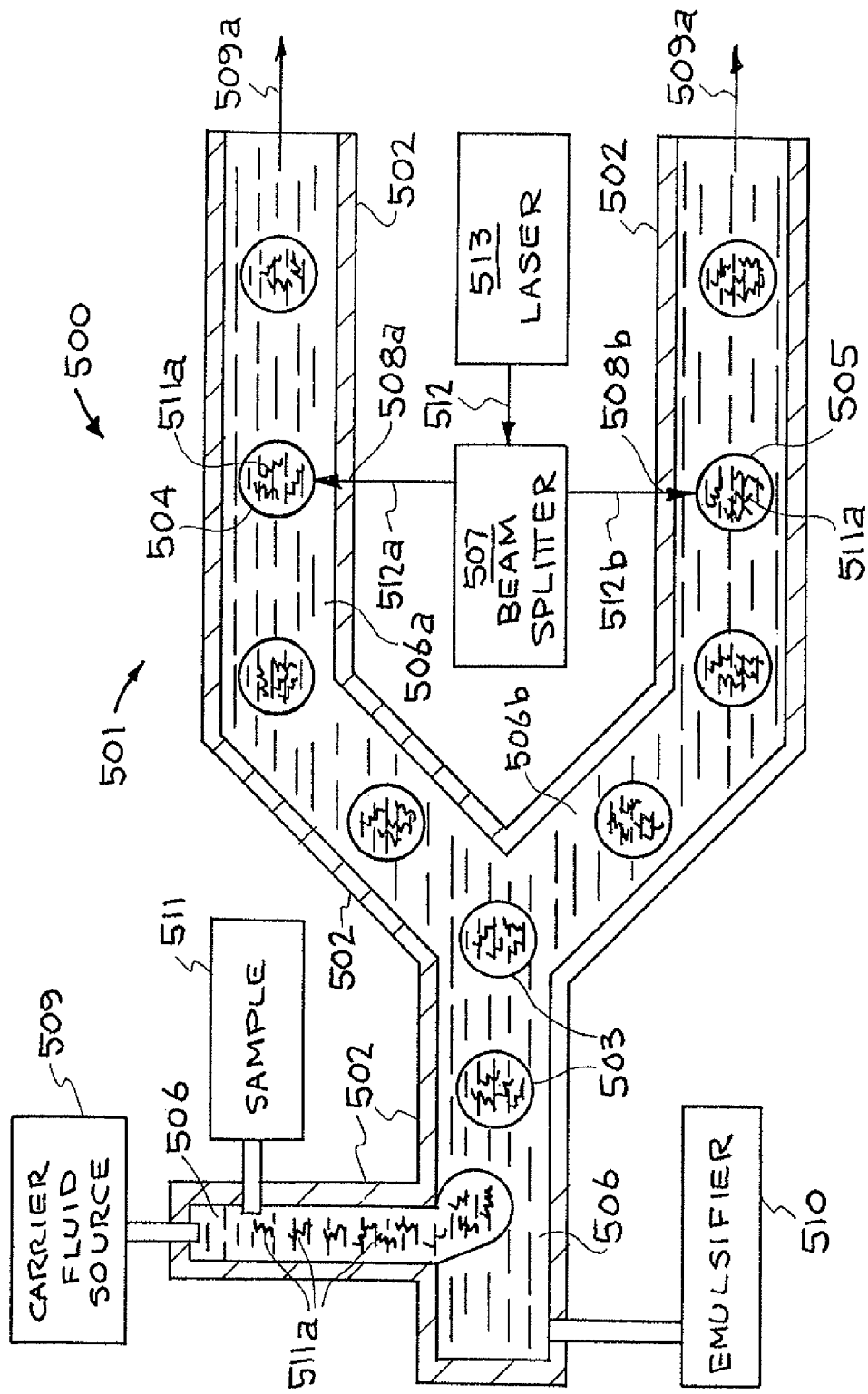
FIG. 5 illustrates another embodiment of the present invention.

Referring now to FIG. 5, another embodiment of a system constructed in accordance with the present invention is illustrated. This system is designated generally by the reference numeral 500. The system 500 provides extremely rapid and efficient heating of a sample 511 in a micro-optical-electro-mechanical system (MOEMS) device 501. The device 501 includes a main microchannel flow channel 506, a first branch microchannel flow channel 506a, and a second branch microchannel flow channel 506b. The microchannel flow channels 506, 506a, and 506b are contained within silicon or glass walls 502.

The sample 511a to be analyzed is introduced to the microchannel flow channels 506, 506a, and 506b by a droplet maker or other device that produces droplets or microreactors 503, 504, 505. An example of a droplet maker is shown in U.S. Published Patent Application No. 2008/0166793 for sorting, amplification, detection, and identification of nucleic acid subsequences Neil R. Beer et al published Jul. 10, 2008. U.S. Published Patent Application No. 2008/0166793 for sorting, amplification, detection, and identification of nucleic acid subsequences Neil R. Beer et al published Jul. 10, 2008 is incorporated herein by reference. The sample 511a can be bacterial cells, virus particles, nucleic acids, proteins, biomolecules, chemical agents, explosives agents, and other targets of interest. A source 511 of the sample 511a is connected to introduce the sample into the microchannel flow channels 506, 506a, and 506b. The sample 511a is contained within the droplets or microreactors 503, 504, 505.

The droplet maker produces the droplets or microreactors 503, 504, 505 containing the sample 511. A carrier fluid 509a designated by the arrows moves the droplets or microreactors 503, 504, 505 through the microchannel flow channel 506. The carrier fluid 509a can be oil, Fluorinert, water, or other carrier fluid. The carrier fluid 509a is introduced into the microchannel flow channels 506, 506a, and 506b by the carrier fluid source 509. The droplets or microreactors 503, 504, 505 containing the sample 511a are carried to areas where they will be heated by a laser 513. An emulsifier 510 can be introduced into the microchannel flow channels 506, 506a, and 506b and into contact with the carrier fluid 509a.

The laser 513 transmits a laser beam 512 to a beam splitter 507. The beam splitter 507 splits the laser beam 512 into two separate laser beams 512a and 512b. The two separate laser beams 512a and 512b are directed to the microchannel flow channels 506a and 506b respectively.

The laser beam 512a is directed through the wall 502 of the microchannel flow channel 506a in a heating area 508a. The laser beam 512a provides spot-focused heating of the droplet or microreactor 504 containing and the sample 511a. The silicon or glass wall 502, as well as any non-aqueous sheathing flow, are not appreciably heated by the laser beam 512a.

The laser beam 512b is directed through the wall 502 of the microchannel flow channel 506b in a heating area 508b. The laser beam 512b provides spot-focused heating of the droplet or microreactor 505 containing and the sample 511a. The silicon or glass wall 502, as well as any non-aqueous sheathing flow, are not appreciably heated by the laser beam 512b.

The structural details of the system 500 having been described, the operation of the system 500 will be explained. The carrier fluid 509a and emulsified droplets 503, 504, 505 are injected into the flow channels 506, 506a, and 506b. The emulsified droplets 503, 504, 505 act as individual chemical reactors. The laser 513 directs laser beam 512 to beam splitter 507. The beam splitter 507 splits the laser beam 512 into two separate laser beams 512a and 512b. The two separate laser beams 512a and 512b are directed to the microchannel flow channel 506a and 506b respectively. The laser beams 512a and 512b are directed through the walls 502 of the microchannel flow channels 506a and 506b in the heating areas 508a and 508b respectively. The laser beams 512a and 512b provide spot-focused heating of the droplets or microreactors 504 and 505 and the sample 511a. The silicon or glass wall 502, as well as any non-aqueous sheathing flow, are not appreciably heated by the laser beams 512a and 512b. The laser 513 is operated in continuous mode or pulsed, and delivers enough energy to the sample 511a instantaneously heat the sample 511a while not heating any carrier fluid, entrapped air, or the silicon or glass wall 502.

Figure 6:
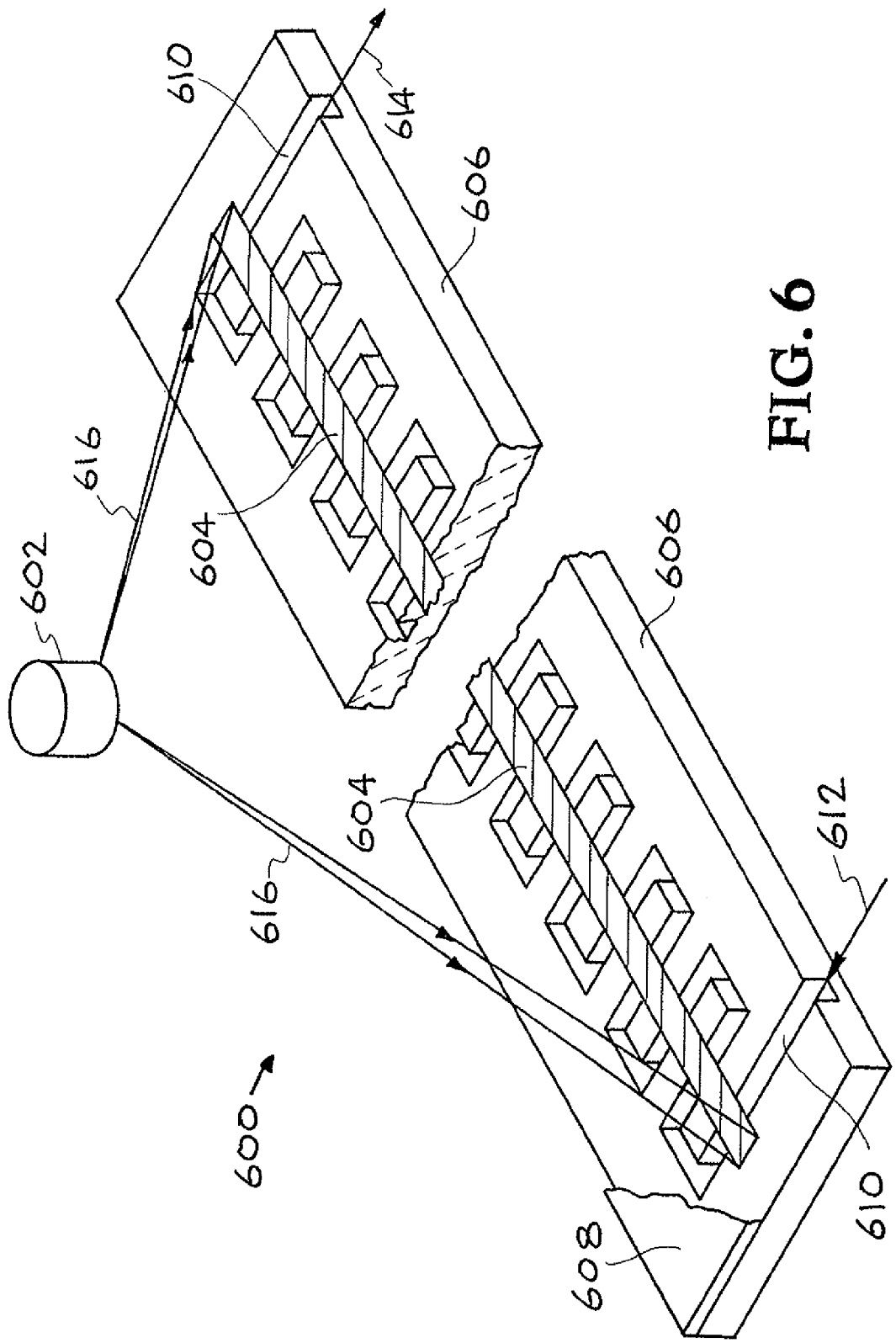
FIG. 6 illustrates another embodiment of the present invention.

Referring now to FIG. 6, another embodiment of a system constructed in accordance with the present invention is illustrated. The system is designated generally by the reference numeral 600. The system 600 utilizes a serpentine micro fluid channel 610 and an optical system 602 to provide extremely rapid and efficient heating of aqueous solutions within continuous streams or segmented microdroplets in a micro-optical-electro-mechanical system (MOEMS) device.

The system 600 includes an etched serpentine microchannel flow channel 610 contained within a micro chip 606. A transparent cover 608 is positioned over the serpentine microchannel flow channel 610. A carrier fluid source introduces a carrier fluid into the serpentine microchannel flow channel 610 through inlet 612. The sample to be analyzed is carried through the serpentine microchannel flow channel 610 by the carrier fluid. The sample can be bacterial cells, virus particles, nucleic acids, proteins, biomolecules, chemical agents, explosives agents, and other targets of interest. The sample is carried through a heating area 604 (optical output footprint) by the carrier fluid. The optical system 602 transmits a beam 616 to the heating area optical output footprint 604. The silicon or glass elements, as well as any non-aqueous sheathing flow, are not appreciably heated. The sample to be analyzed is moved from the serpentine microchannel flow channel 610 by the outlet 614.

Referring again to FIG. 6, the operation of the system 600 will be described. Sheathing fluid and the sample are injected into the flow channel 610 through inlet 612. The optical system 602 transmits the beam of energy to the heating area or optical output footprint 604 of the serpentine microchannel flow channel 610. The optical system 602 is operated in continuous mode or pulsed, and delivers enough energy to the aqueous contents of the channel 610 to instantaneously heat the sample while not heating any carrier fluid, entrapped air, or the silicon or glass substrate of the micro chip 606 itself.

Figure 7A:
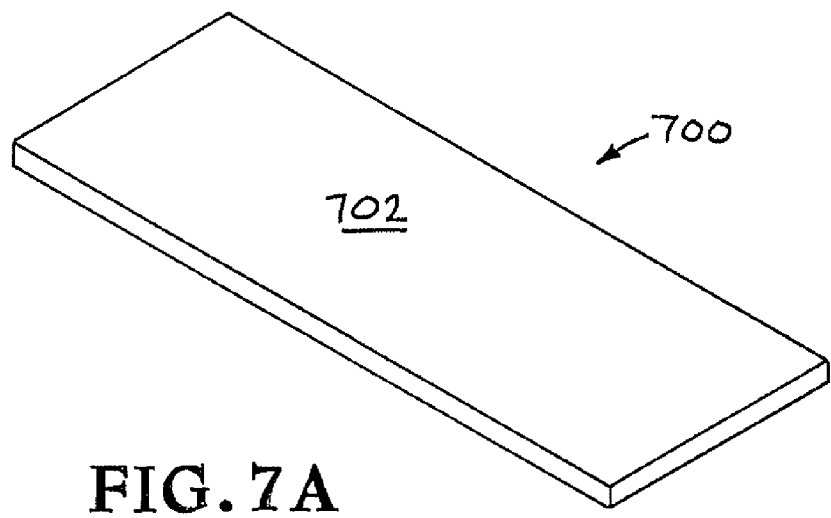
FIG. 7 illustrates another embodiment of the present invention.
Figure 7B:
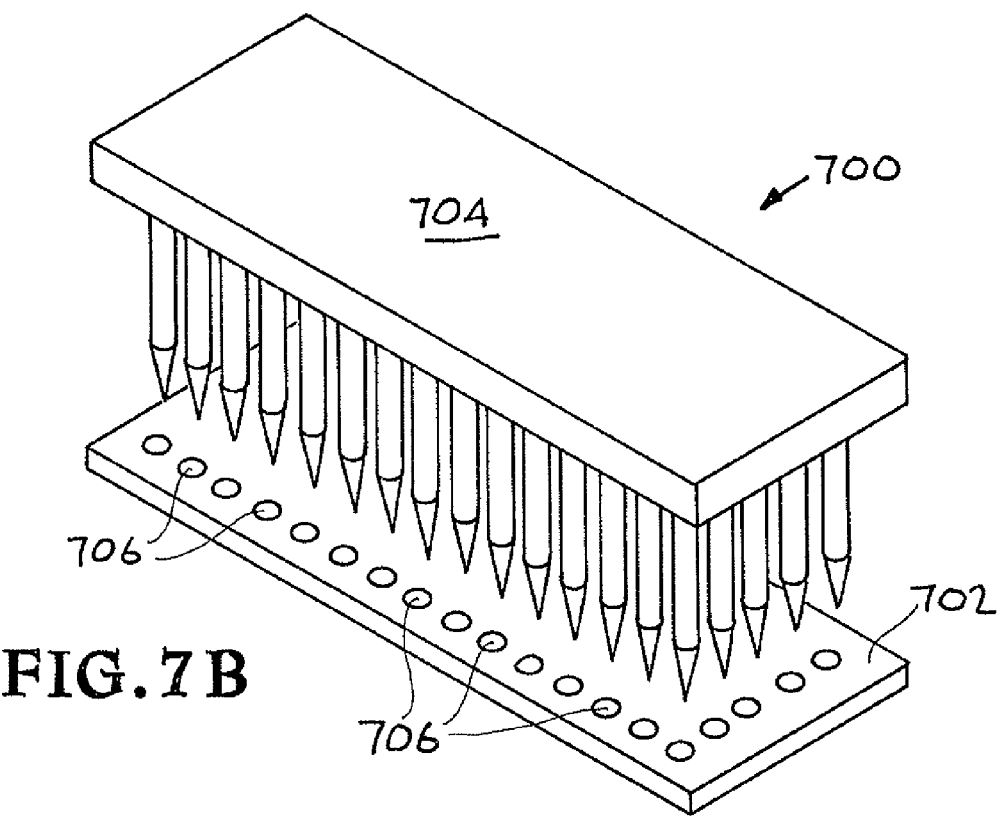

Referring now to FIGS. 7A through 7F, another embodiment of a system constructed in accordance with the present invention is illustrated. The system is designated generally by the reference numeral 700. Referring to FIG. 7A, a glass or polymer microarray slide (701) contains up to ten million individual clusters or "spots", each of which contains approximately 100,000 identical nucleic acid probes attached on the same end to the microarray surface (702). Referring now to FIG. 7B a spot creation system 704 of the prior art is shown that allows spots 706 to be accurately positioned on the glass or polymer microarray slide (701).

Figure 7C:
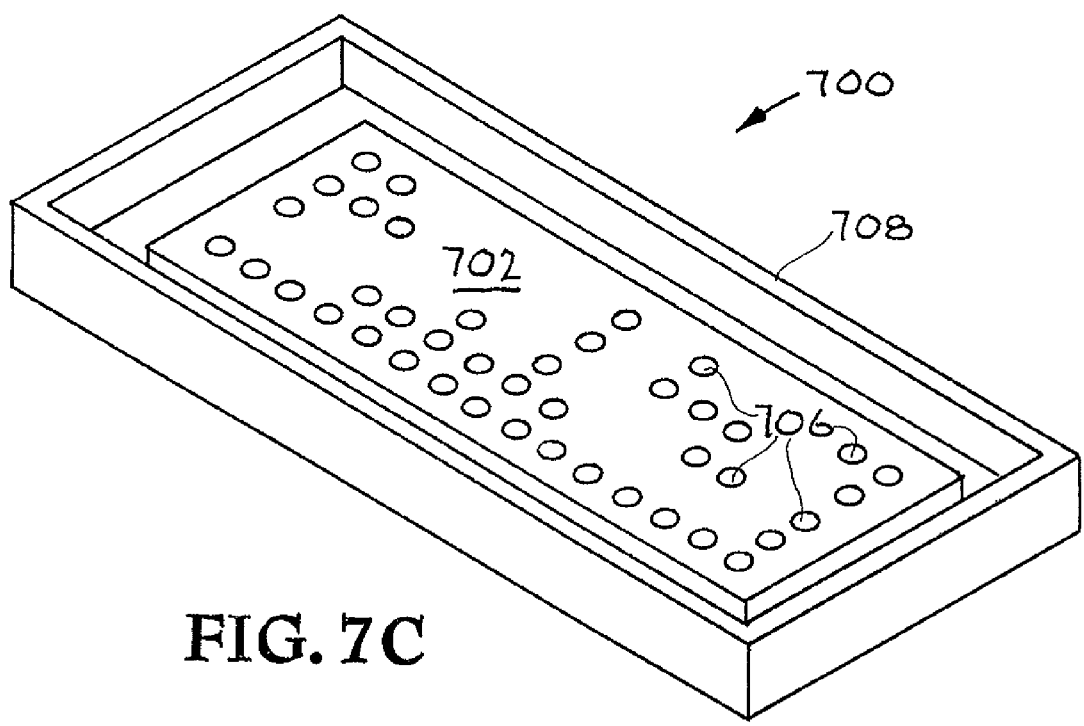

Referring now to FIG. 7C, a hybridization and PCR flow cell (708) contains the nucleic acid sample to be detected in solution. The solution is pumped over the microarray surface (702), and nucleic acid DNA or RNA to be detected binds or "hybridizes" to individual probe spots (706) at the locations corresponding to their corresponding complementary sequence. Since each probe spot (706) on the microarray surface (702) inside the hybridization and flow cell (708) has up to approximately 100,000 or more identical nucleic acid probes, Polymerase Chain Reaction (PCR) reagents can be washed over the microarray surface (702) to perform amplification at spots (706) that have bound "hybridized" target sequences if the spots to be amplified are appropriately thermal cycled to power the PCR process.

Figure 7D:
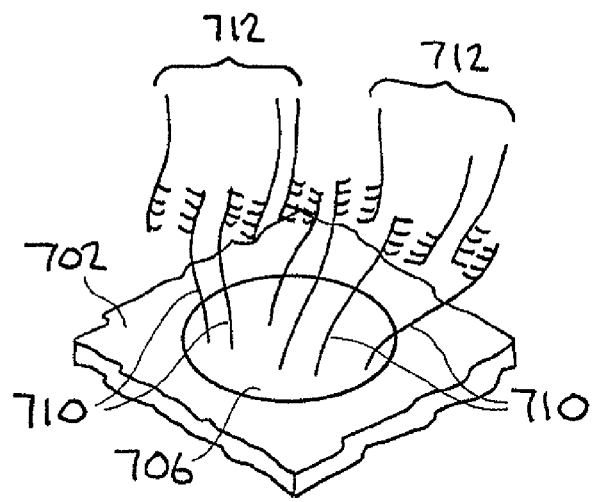

Referring now to FIG. 7D, a probe spot (706) contains a high density of identical nucleic acid probes (710) bound through linkers to the microarray surface (702). The desired target sequences to be detected (712) hybridize under appropriate pH and thermal conditions to their complementary probes (710), allowing either optical detection through fluorescent reporters (chemically bound to the target sequences prior to washing over the array), or amplification in the hybridization and PCR flow cell (708). Amplification methods common in the art such as "Bridge amplification" are ideal, and could be performed by optically-induced thermal cycling of the entire array, or of individual spots. Briefly, the method of Bridge Amplification is summarized below.

1. Prepare Genomic DNA Sample: Randomly fragment genomic DNA and ligate adapters to both ends of the fragments.
2. Attach DNA to Surface: Add unlabeled nucleotides and enzyme to initiate solid-phase bridge amplification.
3. Bridge Amplification: Bind single-stranded fragments randomly to the inside surface of the flow cell channels or the microarray surface.
4. Fragments Become Double-Stranded: The enzyme incorporates nucleotides to build double-stranded bridges on the solid-phase substrate.
5. Denature the Double-Stranded Molecules: Denaturation leaves single-stranded templates anchored to the substrate.
6. Complete Amplification Several million dense clusters of double-stranded DNA are generated in each channel of the flow cell or the microarray surface.

This technique allows much faster amplification than is currently possible, and enables faster sequencing of genomic targets.

Figure 7E:
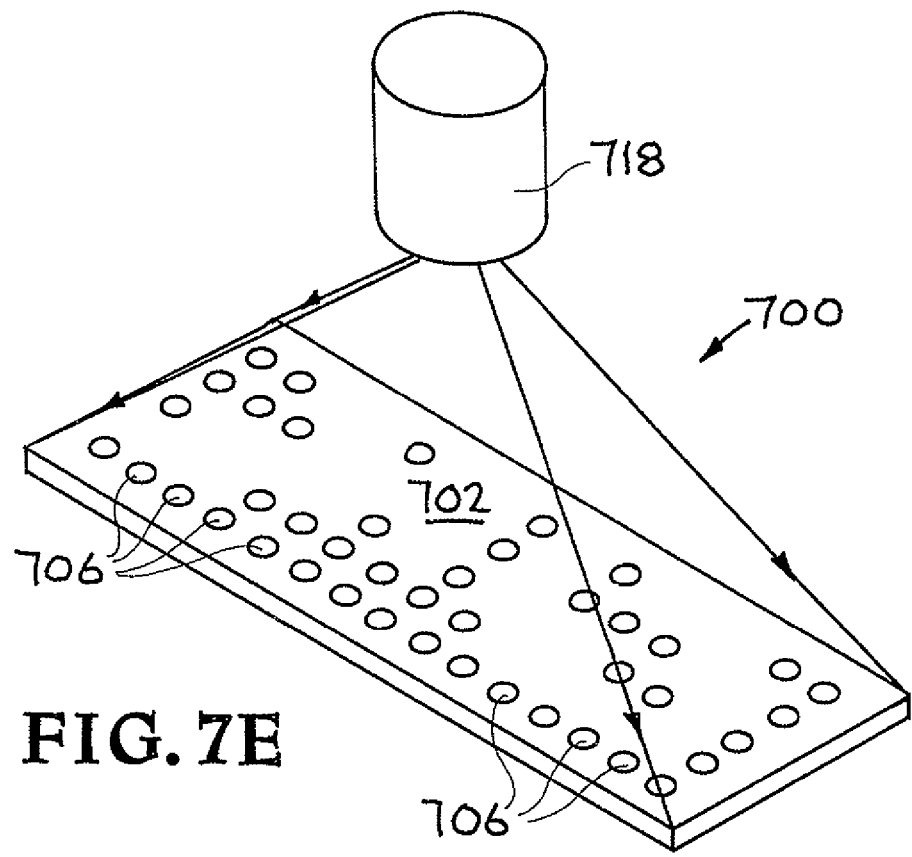

Referring now to FIG. 7E, the probe spots (706) on the microarray surface (702) are illuminated under optical radiation from the light source and beam delivery system (718). Light rays cover the entire array, and due to optical energy absorption in the aqueous layer occurring under Beer's Law, thermal cycling or heating every spot on the array surface (702). This enables chemical reactions on the microarray surface (702) such as PCR, bridge amplification PCR, oligonucleotide probe and target template (710) & (712) denaturation, and protein folding or other protein-based reactions for applications such as immunoassay microarrays.

Figure 7F:
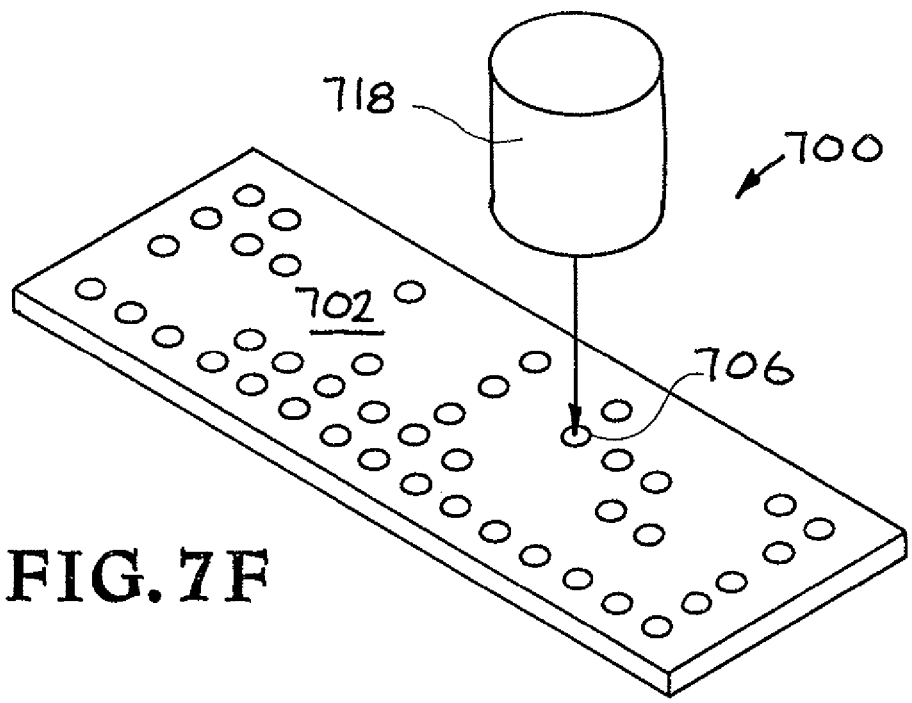

Referring now to FIG. 7F, individually selected probe spots (706) on the microarray surface (702) are illuminated under optical radiation from the light source and beam delivery system (718). Light rays are directed to an individual probe spot (706) and due to optical energy absorption in the aqueous layer occurring under Beer's Law, thermal cycling or heating of individual probe spot (706) on the array surface (702) is accomplished. The steps are repeated for other individual probe spots (706). This enables chemical reactions on the microarray surface (702) such as PCR, bridge amplification PCR, oligonucleotide probe and target template (710) & (712) denaturation, and protein folding or other protein-based reactions for applications such as immunoassay microarrays.

Referring again to FIGS. 7A through 7F, the operation of the system 700 will be described. A glass or polymer microarray slide (701) contains up to ten million individual clusters or "spots", each of which contains approximately 100,000 identical nucleic acid probes attached on the same end to the microarray surface (702). A hybridization and PCR flow cell (708) contains the nucleic acid sample to be detected in solution. The solution is pumped over the microarray surface (702), and nucleic acid DNA or RNA to be detected binds or "hybridizes" to individual probe spots (706) at the locations corresponding to their corresponding complementary sequence. Since each probe spot (706) on the microarray surface (702) inside the hybridization and flow cell (708) has up to approximately 100,000 or more identical nucleic acid probes, Polymerase Chain Reaction (PCR) reagents can be washed over the microarray surface (702) to perform amplification at spots (706) that have bound "hybridized" target sequences if the spots to be amplified are appropriately thermal cycled to power the PCR process. A probe spot (706) contains a high density of identical nucleic acid probes (710) bound through chemical linkers (many different chemistries are common in the art) to the microarray surface (702). The desired target sequences to be detected (712) hybridize under appropriate pH and thermal conditions to their complementary probes (710), allowing either optical detection through fluorescent reporters (chemically bound to the target sequences prior to washing over the array), or amplification in the hybridization and PCR flow cell (708). Amplification methods common in the art such as "Bridge amplification" are ideal, and are performed by optically-induced thermal cycling of the entire array, or of individual spots. Individually selected probe spots (706) or the entire microarray surface (702) are illuminated under optical radiation from the light source and beam delivery system (718). Light rays cover the entire array or individual spots depending on positioning and focusing of the optical delivery system which can include either pointing motors and/or a scanning translational XY stage holding the microarray (700) and hybridization flow cell (708), and due to optical energy absorption in the aqueous layer occurring under Beer's Law, thermal cycling or heating every spot on the array surface (702). This enables chemical reactions on the microarray surface (702) such as PCR, bridge amplification PCR, oligonucleotide probe and target template (710) & (712) denaturation, and protein folding or other protein-based reactions for applications such as immunoassay microarrays.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A micro-optical-electro-mechanical system apparatus for heating of a sample comprising:
   a microchip;
   a microchannel flow channel in said microchip, said microchannel flow channel containing the sample;
   a laser that directs a laser beam onto the sample for heating the sample;
   a beam splitter for splitting said laser beam into a multiplicity of laser beams;
   a wall section of said microchannel flow channel that receives said multiplicity of laser beams and enables said laser beams to pass through wall section of said microchannel flow channel, said wall section said microchannel flow channel being made of a material that is not appreciably heated by said laser beams, wherein said multiplicity of laser beams pass through wall section of said microchannel flow channel and heat the sample;

a carrier fluid within said microchannel flow channel for moving the sample in said microchannel flow channel, said carrier fluid being made of a material that is not appreciably heated by said laser beams; wherein said laser beams pass through wall section of said microchannel flow channel and heat the sample.

2. A micro-optical-electro-mechanical system apparatus for heating of a sample comprising a microchip;

a microchannel flow channel in said microchip, said microchannel flow channel containing the sample, wherein said microchannel flow channel includes a multiplicity of individual microchannel flow channels each of which have wall sections;

a laser that directs a laser beam onto the sample for heating the sample;

a beam splitter for splitting said laser beam into a multiplicity of laser beams wherein said multiplicity of laser beams pass through wall sections of said multiplicity of individual microchannel flow channels for heating the sample wherein said wall sections receive said laser beams and enable said laser beams to pass through wall sections of said multiplicity of individual microchannel flow channels, said wall sections being made of a material that is not appreciably heated by said laser beams;

a carrier fluid within said multiplicity of individual microchannel flow channels for moving the sample in said multiplicity of individual microchannel flow channels, said carrier fluid being made of a material that is not appreciably heated by said laser beams; wherein said laser beams pass through wall section of said multiplicity of individual microchannel flow channels and heat the sample.

* * * * *